(12) United States Patent
Callender et al.

(10) Patent No.: US 12,194,120 B2
(45) Date of Patent: Jan. 14, 2025

(54) SKIN CARE FORMULATION CONTAINING SILVER NANOPARTICLES

(71) Applicant: HEIDI SKIN, LLC, Scottsdale, AZ (US)

(72) Inventors: Heidi Callender, Scottsdale, AZ (US); Holly Nolan, Kirtland, OH (US)

(73) Assignee: HEIDI SKIN, LLC, Scottsdale, AZ (US)

( * ) Notice: Subject to any disclaimer, the term of this patent is extended or adjusted under 35 U.S.C. 154(b) by 68 days.

(21) Appl. No.: 17/890,947

(22) Filed: Aug. 18, 2022

(65) Prior Publication Data
US 2023/0404866 A1   Dec. 21, 2023

Related U.S. Application Data

(60) Provisional application No. 63/347,146, filed on May 31, 2022.

(51) Int. Cl.

| | |
|---|---|
| *A61K 8/19* | (2006.01) |
| *A61K 8/64* | (2006.01) |
| *A61K 8/67* | (2006.01) |
| *A61K 8/73* | (2006.01) |
| *A61K 8/9794* | (2017.01) |
| *A61K 9/51* | (2006.01) |
| *A61K 31/355* | (2006.01) |
| *A61K 31/375* | (2006.01) |
| *A61K 31/728* | (2006.01) |
| *A61K 33/38* | (2006.01) |
| *A61K 36/886* | (2006.01) |
| *A61K 36/888* | (2006.01) |
| *A61K 38/06* | (2006.01) |
| *A61P 17/02* | (2006.01) |
| *A61Q 19/00* | (2006.01) |
| *A61Q 19/08* | (2006.01) |

(52) U.S. Cl.
CPC .............. *A61K 8/19* (2013.01); *A61K 8/64* (2013.01); *A61K 8/676* (2013.01); *A61K 8/678* (2013.01); *A61K 8/735* (2013.01); *A61K 8/9794* (2017.08); *A61K 9/51* (2013.01); *A61K 31/355* (2013.01); *A61K 31/375* (2013.01); *A61K 31/728* (2013.01); *A61K 33/38* (2013.01); *A61K 36/886* (2013.01); *A61K 36/888* (2013.01); *A61K 38/06* (2013.01); *A61P 17/02* (2018.01); *A61Q 19/005* (2013.01); *A61Q 19/007* (2013.01); *A61Q 19/08* (2013.01); *A61K 2800/412* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 9,795,550 B2 | 10/2017 | Hood et al. | |
| 10,434,052 B2 | 10/2019 | Hood et al. | |
| 10,675,234 B1 * | 6/2020 | Caires | A61K 8/36 |
| 10,722,461 B2 | 7/2020 | Burnam | |
| 10,966,927 B2 | 4/2021 | Burnam | |
| 11,071,786 B2 | 7/2021 | Latta | |
| 11,077,046 B2 | 8/2021 | Hood et al. | |
| 11,564,395 B2 * | 1/2023 | Moeller | A61Q 17/04 |
| 2010/0021563 A1 * | 1/2010 | Levesque | A61K 33/30 |
| | | | 424/642 |
| 2021/0000728 A1 * | 1/2021 | Kelly | A61K 8/9789 |
| 2021/0127682 A1 * | 5/2021 | Moeller | A01N 59/16 |
| 2021/0346276 A1 * | 11/2021 | Mitchell | A61K 8/987 |
| 2023/0190620 A1 * | 6/2023 | Motahari | A61K 8/675 |
| | | | 424/401 |

FOREIGN PATENT DOCUMENTS

| | | |
|---|---|---|
| WO | 2014186399 A1 | 11/2014 |
| WO | 2020252440 A2 | 12/2020 |
| WO | WO-2022224380 A1 * | 10/2022 |

OTHER PUBLICATIONS

PubChem "Alpha-Tocopherol Acetate" (https://pubchem.ncbi.nlm.nih.gov/compound/86472; accessed Oct. 2, 2023) (Year: 2023).*
Tudose et al., Regenerative properties of aloe vera juice on human keratinocyte cell culture, Jan. 2009FARMACIA 57(5):590-597 (Year: 2009).*
Wakshlak RB, Pedahzur R, Avnir D. Antibacterial activity of silver-killed bacteria: the "zombies" effect. Sci Rep. Apr. 23, 2015;5:9555. doi: 10.1038/srep09555. PMID: 25906433; PMCID: PMC5386105.
Iroha, I. R., Esimone, C.O. and Imomoh, O. O. Antibacterial efficacy of colloidal silver alone and in combination with other antibiotics on isolates from wound Infections. Scientific Research and Essay vol. 2 (8), pp. 338-341, Aug. 2007.
URL:<https://www.niehs.nih.gov/health/topics/agents/aloe>; National Institute of Environmental Health Sciences, Aloe Vera, retrieved Dec. 27, 2023; (5 pages).
Seltenrich N. Nanosilver: weighing the risks and benefits. Environ Health Perspect. Jul. 2013;121(7):A220-5. doi: 10.1289/ehp.121-a220. PMID: 23816826; PMCID: PMC3702006.
Chung IM, Park I, Seung-Hyun K, Thiruvengadam M, Rajakumar G. Plant-Mediated Synthesis of Silver Nanoparticles: Their Characteristic Properties and Therapeutic Applications. Nanoscale Res Lett. Dec. 2016;11(1):40. doi: 10.1186/S11671-016-1257-4. Epub Jan. 28, 2016. PMID: 26821160; PMCID: PMC4731379.

(Continued)

*Primary Examiner* — Tigabu Kassa
(74) *Attorney, Agent, or Firm* — Quarles & Brady LLP

(57) ABSTRACT

The present disclosure provides a skin care formulation, which includes silver nanoparticles (AgNPs) and/or silver microparticles (AgMPs), vitamin E, glycerin, hyaluronic acid or a salt thereof, and water. The skin care formulation may be in a form of a serum. The present formulation may be used for treating a skin condition, such as aging, wrinkle, or pigmentation. The present formulation also may be used for moisturizing, rejuvenating, repairing, or improving aesthetic appearance of a skin of a subject in need thereof.

14 Claims, No Drawings

(56) References Cited

OTHER PUBLICATIONS

Feng, Q.L., Wu, J., Chen, G.Q., Cui, F.Z., Kim, T.N. and Kim, J.O. (2000), A mechanistic study of the antibacterial effect of silver ions on Escherichia coli and Staphylococcus aureus. J. Biomed. Mater. Res., 52: 662-668. https://doi.org/10.1002/1097-4636(20001215)52:4<662:: AID-JBM10>3.0.CO;2-3.
Schagen, S.K. Topical Peptide Treatments with Effective Anti-Aging Results. Cosmetics 2017, 4, 16. https://doi.org/10.3390/cosmetics4020016.
Resende DISP, Ferreira MS, Sousa-Lobo JM, Sousa E, Almeida IF. Usage of Synthetic Peptides in Cosmetics for Sensitive Skin. Pharmaceuticals (Basel). Jul. 21, 2021;14(8):702. doi: 10.3390/ph14080702. PMID: 34451799; PMCID: PMC8400021.
Klein T, Bischoff R. Physiology and pathophysiology of matrix metalloproteases. Amino Acids. Jul. 2011;41(2):271-90. doi: 10.1007/s00726-010-0689-x. Epub Jul. 18, 2010. PMID: 20640864; PMCID: PMC3102199.
Avcil, M, Akman, G, Klokkers, J, Jeong, D, Çelik, A. Efficacy of bioactive peptides loaded on hyaluronic acid microneedle patches: A monocentric clinical study. J Cosmet Dermatol. 2019; 19: 328-337. https://doi.org/10.1111/jocd.13009.
Derek McPhee, Armelle Pin, Lance Kizer, and Loren Perelman, Squalane from Sugarcane, Cosmetics & Toiletries magazine, vol. 129, No. 6, Jul./Aug. 2014.
Mármol I, Sánchez-de-Diego C, Jiménez-Moreno N, Ancin-Azpilicueta C, Rodríguez-Yoldi MJ. Therapeutic Applications of Rose Hips from Different Rosa Species. Int J Mol Sci. May 25, 2017;18(6):1137. doi: 10.3390/ijms18061137. PMID: 28587101; PMCID: PMC5485961.
David E. Kleiner, William G. Stetler-Stevenson, Structural biochemistry and activation of matrix metalloproteases, Current Opinion in Cell Biology, vol. 5, Issue 5, 1993, pp. 891-897.
URL: <https://health.clevelandclinic.org/rosehip-oil-benefits-for-skin-and-hair/>; Cleveland Clinic, The Benefits of Rose Hip Oil, retrieved Dec. 27, 2023; (6 pages).
Moghimipour, Eskandar & Siahpoosh, Amir & Yaghoobi, Reza & Malayeri, Alireza & Faramarzi, Fatemeh. (2012). Clinical trial of a herbal topical cream in treatment of Acne vulgaris. American Journal of PharmTech Research. 2. 263-271.
URL: <https://www.medicalnewstoday.com/articles/326931#side-effects>; MedicalNewsToday, Rosehip oil: Benefits and how to use it on the face, retrieved Dec. 27, 2023; (19 pages).
Iliopoulos F, Sil BC, Moore DJ, Lucas RA, Lane ME. 3-O-ethyl-l-ascorbic acid: Characterisation and investigation of single solvent systems for delivery to the skin. Int J Pharm X. Jul. 19, 2019;1:100025. doi: 10.1016/j.ijpx.2019.100025. PMID: 31517290; PMCID: PMC6733298.
Wilma F. Bergfeld; Donald V. Belsito; Ronald A. Hill; Curtis D. Klaassen; Daniel C. Liebler; James G. Marks, Jr.; Ronald C. Shank; Thomas J. Slaga; Paul W. Snyder, Lillian J. Gill, and Lillian C. Becker, Safety Assessment of Glycerin as Used in Cosmetics, Cosmetic Ingredient Review, Release Date: Aug. 18, 2014.
Papakonstantinou E, Roth M, Karakiulakis G. Hyaluronic acid: A key molecule in skin aging. Dermatoendocrinol. Jul. 1, 2012;4(3):253-8. doi: 10.4161/derm.21923. PMID: 23467280; PMCID: PMC3583886.
Baumann, L. (2007), Skin ageing and its treatment. J. Pathol., 211: 241-251. https://doi.org/10.1002/path.2098.
Bernstein, E.F., Underhill, C.B., Hahn, P.J., Brown, D.B. and Uitto, J. (1996), Chronic sun exposure alters both the content and distribution of dermal glycosaminoglycans. British Journal of Dermatology, 135: 255-262; https://doi.org/10.1111/j.1365-2133.1996.tb01156.x.
I Ghersetich, T Lotti, G Campanile, C Grappone, G Dini, Hyaluronic acid in cutaneous intrinsic aging, International journal of dermatology, 1994.
Paul H. Weigel, Gerald M. Fuller, Robert D. LeBoeuf, A model for the role of hyaluronic acid and fibrin in the early events during the inflammatory response and wound healing, Journal of Theoretical Biology, vol. 119, Issue 2, 1986, pp. 219-234, ISSN 0022-5193, https://doi.org/10.1016/S0022-5193(86)80076-5.
Peter Teriete, Suneale Banerji, Martin Noble, Charles D. Blundell, Alan J. Wright, Andrew R. Pickford, Edward Lowe, David J. Mahoney, Markku I. Tammi, Jan D. Kahmann, Iain D. Campbell, Anthony J. Day, David G. Jackson, Structure of the Regulatory Hyaluronan Binding Domain in the Inflammatory Leukocyte Homing Receptor CD44, Molecular Cell, vol. 13, Issue 4, 2004, pp. 483-496, ISSN 1097-2765, https://doi.org/10.1016/S1097-2765(04)00080-2.
Michalak M, Pierzak M, Kręcisz B, Suliga E. Bioactive Compounds for Skin Health: A Review. Nutrients. Jan. 12, 2021;13(1):203. doi: 10.3390/nu13010203. PMID: 33445474; PMCID: PMC7827176.
Mônica Manela-Azulay, Ediléia Bagatin, Cosmeceuticals vitamins, Clinics in Dermatology, vol. 27, Issue 5, 2009, pp. 469-474, ISSN 0738-081X, https://doi.org/10.1016/j.clindermatol.2009.05.010.
Lee, G.Y.; Han, S.N. The Role of Vitamin E in Immunity. Nutrients 2018, 10, 1614. https://doi.org/10.3390/nu10111614.
Kunicka-Styczyńska, A., Sikora, M. and Kalemba, D. (2009), Antimicrobial activity of lavender, tea tree and lemon oils in cosmetic preservative systems. Journal of Applied Microbiology, 107: 1903-1911, https://doi.org/10.1111/j.1365-2672.2009.04372.x.
URL: https://www.byrdie.com/silver-skincare, Byrdie, "Silver in Skincare: What's It All About?"; Chloe Burcham, Apr. 21, 2021, retrieved Dec. 27, 2023; (7 pages).
URL: https://health.clevelandclinic.org/whats-causing-your-crepey-skin-and-how-can-you-fix-it/; Cleveland Clinic, "Crepey Skin? A Surprising Cause—and 4 Expert Fixes", retrieved Dec. 27, 2023; (## pages).
Jegasothy SM, Zabolotniaia V, Bielfeldt S. Efficacy of a New Topical Nano-hyaluronic Acid in Humans. J Clin Aesthet Dermatol. Mar. 2014;7(3):27-9. PMID: 24688623; PMCID: PMC3970829.
Swindell WR, Randhawa M, Quijas G, Bojanowski K, Chaudhuri RK. Tetrahexyldecyl Ascorbate (THDC) Degrades Rapidly under Oxidative Stress but Can Be Stabilized by Acetyl Zingerone to Enhance Collagen Production and Antioxidant Effects. Int J Mol Sci. Aug. 15, 2021;22(16): 8756. doi: 10.3390/ijms22168756. PMID: 34445461; PMCID: PMC8395926.
URL: <https://www.mayoclinic.org/diseases-conditions/rosacea/symptoms-causes/syc-20353815>; Mayo Clinic, "Rosacea", retrieved Dec. 27, 2023; (9 pages).
URL: <https://www.everydayhealth.com/photogalerty/cities-tough-on-skin-aspx>; Everyday Health Group, "Skin & Beauty", retrieved Dec. 27, 2023; (12 pages).
URL: <https://thesilveredge.com/tem-image/>, The Silver Edge; "See the Micro-Particle Colloidal Silver Difference for Yourself . . ."; retrieved Dec. 27, 2023; (9 pages).
URL: <https://www.lookfantastic.com/blog/discover/colloidal-silver-beauty/>; LookFantastic; "An edit of the best silver-infused beauty products", retrieved Dec. 27, 2023; (9 pages).
URL: <https://amazingy.com/en/argentum-skin-care-order-europe-germany.html>; Amazingy—Flowing Cosmetics GmbH, "ARgENTUM apothecary—Unique & Powerful Skin", retrieved Dec. 27, 2023; (9 pages).
URL: <https://amazingy.com/en/yuli-skincare-order-europe-online-shop.html>; Flowing Cosmetics GmbH, "YÜLI Skincare" retrieved Dec. 27, 2023; (10 pages).
URL: <https://www.omorovicza.com/silver-skin-saviour/11836727.html>; Omorovicza, Budapest, "Silver Skin Saviour", retrieved Dec. 27, 2023; (15 pages).
Yoo J, Park K, Yoo Y, Kim J, Yang H, Shin Y. Effects of Egg Shell Membrane Hydrolysates on Anti-Inflammatory, Anti-Wrinkle, Anti-Microbial Activity and Moisture-Protection. Korean J Food Sci Anim Resour. 2014;34(1):26-32. doi: 10.5851/kosfa.2014.34.1.26. Epub Feb. 28, 2014. PMID: 26760742; PMCID: PMC4597828.
Dilshad et al., "Synthesis of Functional Silver Nanoparticles and Microparticles with Modifiers and Evaluation of Their Antimicrobial, Anticancer, and Antioxidant Activity," Journal of Functional Biomaterials, 2020, 11(4), 76.

(56) References Cited

OTHER PUBLICATIONS

Khadangi, F. and Azzi, A. (2019), Vitamin E—The Next 100 Years. IUBMB Life, 71: 411-415. https://doi.org/10.1002/iub. 1990.

* cited by examiner

SKIN CARE FORMULATION CONTAINING SILVER NANOPARTICLES

CROSS-REFERENCE TO RELATED APPLICATIONS

This application claims priority to U.S. Provisional Application No. 63/347,146, filed May 31, 2022, the content of which is hereby incorporated by reference in its entirety.

BACKGROUND

Current skin care products can be expensive and only aim to address one skin problem at a time, e.g., eye bags or crows feet. However, no one product can fix all the skin issues that started to become a reality with age, such as age spots, pigmentation, wrinkles, elasticity loss, moisture loss, UV sun damage, chaffing, dryness, sagging, climate damage, and more. On the other hand, skin damage is a real problem for the entire population, including those caused by sun bathing, swimming, tanning, and many outdoor activities.

Thus, there remains an unmet need for alternative skin care products that can effectively treat multiple skin conditions at reduced cost.

SUMMARY

In one aspect, the present disclosure provides a skin care formulation comprising:
  silver nanoparticles (AgNPs) and/or silver microparticles (AgMPs);
  vitamin E;
  glycerin;
  hyaluronic acid or a salt thereof; and
  water.

In another aspect, provided is a method of treating a skin condition in a subject in need thereof, the method comprising applying an effective amount of a skin care formulation as described herein to the skin of the subject. The skin condition may be, for example, aging, wrinkle, pigmentation, elasticity loss, moisture loss, sun damage, chaffing, dryness, sagging, burns, sores, abrasions, climate damage, scars, eczema, inflammatory dermatitis, skin cancer, or a combination thereof.

In another aspect, the present disclosure provides a method of moisturizing, rejuvenating, repairing, or improving aesthetic appearance of a skin of a subject in need thereof, the method comprising applying an effective amount of a skin care formulation as described herein to the skin of the subject.

DETAILED DESCRIPTION

The present disclosure provides a skin care formulation, in particular a formulation for various skin conditions, such as aging, wrinkle, pigmentation, dryness, and skin damage. The formulation may be applied to the skin of a subject to treat the skin. The formulation may be applied to the skin as a base layer onto which other skin care products may be applied. The present formulation may be characterized by a silver and *Aloe* water base, multi-benefit full-body application, and may dry quickly with a non-greasy matte-silky finish, which are distinguishable from known skin care product. Advantageously, the formulation may be used as a non-greasy, anti-aging body moisturizer with matte finish for men and women of all skin types that dries in under one (1) minute.

Before any embodiments of the invention are explained in detail, it is to be understood that the invention is not limited in its application to the details of construction and the arrangement of components set forth in the following description. The invention is capable of other embodiments and of being practiced or of being carried out in various ways.

Definitions

Unless otherwise defined, all technical and scientific terms used herein have the same meaning as commonly understood by one of ordinary skill in the art. In case of conflict, the present document, including definitions, will control. Suitable methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "comprising," "include(s)," "including," "having," "has," "contain(s)," "containing," and variants thereof, as used herein, are open-ended transitional phrases, terms, or words that are meant to encompass the items listed thereafter and equivalents thereof as well as additional items. The singular forms "a", "and", and "the" include plural references unless the context clearly dictates otherwise. Where the term "comprising" is used, the present disclosure also contemplates other embodiments "comprising," "consisting of," and "consisting essentially of," the embodiments or elements presented herein, whether explicitly set forth or not. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "skin care formulation" as used herein refers to formulations that provide a health or aesthetic benefit to a subject through topical application to the skin of the subject. For example, the formulation may provide treatment of a skin disease or condition.

The term "treatment" as used herein in the context of treating a condition (such as a skin disease or condition), pertains generally to treatment and therapy, whether of a human or an animal (e.g. in veterinary applications), in which a desired therapeutic effect or health benefit is achieved. For example, treatment includes prophylaxis and can ameliorate or remedy the condition, disease, or symptom, or treatment can inhibit the progress of the condition or disease (e.g., reduce the rate of disease/symptom progression or halt the rate of disease/symptom progression).

Composition

In one aspect, the present disclosure provides a skin care formulation comprising:
    silver nanoparticles (AgNPs) and/or silver microparticles (AgMPs);
    vitamin E;
    glycerin;
    hyaluronic acid or a salt thereof; and
    water.

Silver Nanoparticles and/or Silver Microparticles

Silver nanoparticles (AgNPs) and silver microparticles (AgMPs) are a highly effective antibacterial agent. (Dilshad et al., "Synthesis of Functional Silver Nanoparticles and Microparticles with Modifiers and Evaluation of Their Antimicrobial, Anticancer, and Antioxidant Activity," *Journal of Functional Biomaterials*, 2020, 11(4), 76). The shape and size of the silver nanoparticles and/or silver microparticles may be relevant to their antibacterial activity (Chung et al. "Plant-Mediated Synthesis of Silver Nanoparticles: Their Characteristic Properties and Therapeutic Applications," Nanoscale Res Lett. 2016; 11: 40). The broad spectrum antimicrobial activity of silver nanoparticles and silver microparticles may be effectively used as an alternative antimicrobial agent for treatment of septic wounds or burns (Iroha et al., "Antibacterial efficacy of colloidal silver alone and in combination with other antibiotics on isolates from wound Infections," *Scientific Research and Essay*, Vol. 2 (8), pp. 338-341, 2007; Feng et al., "A mechanistic study of the antibacterial effect of silver ions on *Escherichia coli* and *Staphylococcus aureus*," *J Biomed Mater Res.*, 2000, 52(4): 662-8).

The silver nanoparticles and/or silver microparticles may have a circular, spherical, oval, hexagonal, rectangle, triangular, or cubic shape. In some embodiments, the silver nanoparticles and/or silver microparticles have a spherical shape. The silver nanoparticles and/or silver microparticles may have an average size on the scale of nanomers (nm). The average size of the silver nanoparticles and/or silver microparticles may be suitable to provide bioavailable silver to a skin. The size can be, for example, a length, a width, a height, or a diameter of the nanoparticles and/or microparticles. In some embodiments, the size is a diameter of the silver nanoparticles and/or microparticles. In some embodiments, the average size of the silver nanoparticles and/or silver microparticles is about 0.1 nm to about 50 nm, including but not limited to about 0.1 nm to about 30 nm, about 0.1 nm to about 20 nm, about 0.1 nm to about 10 nm, about 0.1 nm to about 5 nm, about 0.1 nm to about 2 nm, about 0.1 nm to about 1 nm, and about 0.5 nm to about 1 nm. In some embodiments, the silver nanoparticles and/or silver microparticles have an average size range of about 0.8 nm to about 50 nm, such as a range of about 0.8 nm to about 40 nm, about 0.8 nm to about 30 nm, about 0.8 nm to about 20 nm, or about 0.8 nm to about 10 nm. For example, the average size of the silver nanoparticles and/or silver microparticles can be about 0.2 nm, 0.5 nm, 0.8 nm, or 1.0 nm. In some embodiments, the average size of the silver nanoparticles and/or silver microparticles is about 0.1 nm to about 2 nm. In some embodiments, the average size of the silver nanoparticles and/or silver microparticles is about 0.8 nm.

The silver nanoparticles and/or silver microparticles may be prepared as a suspension of silver particles in a liquid, such as water or an aqueous medium. The suspension of silver nanoparticles and/or silver microparticles also may be referred to as colloidal silver or silver water. In some embodiments, commercial instrument (e.g., Micro-Particle Colloidal Silver Generator, supplied by The Silver Edge, AZ) may be used to prepare the suspension of silver nanoparticles and/or silver microparticles. The prepared suspension may have a silver concentration of about 1 ppm to about 100 ppm (parts per million), such as about 5 ppm to about 80 ppm, about 5 ppm to about 50 ppm, about 5 ppm to about 40 ppm, about 5 ppm to about 30 ppm, about 5 ppm to about 20 ppm, or about 10 ppm to about 20 ppm. In some embodiments, the prepared suspension has a silver concentration of about 10-20 ppm.

The silver nanoparticles and/or silver microparticles may have a concentration of about 0.1 µg/gram to about 4.0 µg/gram by weight of the skin care formulation. In some embodiments, the silver nanoparticles and/or silver microparticles have a concentration of about 0.5 µg/gram to about 4.0 µg/gram by weight of the skin care formulation, such as about 0.5 µg/gram to about 3.0 µg/gram, about 0.5 µg/gram to about 2.5 µg/gram, about 0.5 µg/gram to about 2.0 µg/gram, about 0.5 µg/gram to about 1.5 µg/gram, or about 0.7 µg/gram to about 2.0 µg/gram. In some embodiments, the silver nanoparticles and/or silver microparticles have a concentration of about 0.5 µg/gram to about 2.0 µg/gram by weight of the skin care formulation. In some embodiments, the silver nanoparticles and/or silver microparticles have a concentration of about 0.7 µg/gram to about 2.0 µg/gram by weight of the skin care formulation, such as about 0.7 µg/gram, about 0.8 µg/gram, about 0.9 jag/gram, about 1.0 jag/gram, about 1.1 µg/gram, about 1.2 µg/gram, about 1.3 µg/gram, about 1.4 jag/gran, about 1.5 µg/gram, about 1.6 µg/gram, about 1.7 µg/gram, about 1.8 µg/gram, about 1.9 µg/gram, or about 2.0 µg/gram.

Vitamin E

Vitamin E may be used to soften skin, reduces appearance of wrinkles and fine lines. Vitamin E has anti-inflammatory properties and may be used to reduces stretch marks, fine lines and scars. It also helps with dermatitis, acne, and eczema; works as a natural anti-aging solution by tightening the skin and keeps it hydrated. Water-insoluble vitamin E may be formed by esterification of acetic acid and tocopherol. The physiologic function of epidermal vitamin E includes contributing to the antioxidant defenses of the skin and protecting the epidermis and dermis against oxidative stress induced by environmental factors. Vitamin E is a major lipid-soluble antioxidant in humans. Owing to the antioxidant properties of vitamin E and its ability to scavenge free radicals and become part of lipid structures, it protects against lipid peroxidation and slows skin aging.

Suitable vitamin E may include any known vitamin E product. In some embodiments, the vitamin E comprises DL-alpha-tocopheryl acetate (e.g., CAS Reg. No. 7695-91-2). The vitamin E may be present in an amount of about 0.1% to about 5% by weight of the skin care formulation. In some embodiments, the vitamin E is about 0.5% to about 5% by weight of the skin care formulation, such as about 0.5% to about 4%, about 0.5% to about 3%, about 0.5% to about 2%, about 0.5%4 to about 1.5%, or about 0.5% to about 1%. In some embodiments, the vitamin E is about 0.5% to about 1.5% by weight of the skin care formulation, such as about 0.5%, about 0.8%, about 0.9%, about 1.0%, about 1.1%, about 1.2%, about 1.3%, about 1.4%, or about 1.5%. In some embodiments, the vitamin E is about 1.1% by weight of the skin care formulation.

Glycerin

Glycerin (e.g., CAS Reg. No. 56-81-5) may moisturize and provide softening and lubricating benefits. Glycerin may be one of the most common and safe ingredients in skincare products. In some embodiments, glycerin as used herein does not contain bovine, ovine, caprine or other animal-derived materials (e.g., 100% vegan). In some embodiments, glycerin as used herein is free of palm oil derivatives.

The glycerin may be present in an amount of about 0.5% to about 5% by weight of the skin care formulation. In some embodiments, the glycerin is about 1% to about 5% by weight of the skin care formulation, such as about 1% to about 4%, about 1% to about 3%, or about 2% to about 3%. In some embodiments, the glycerin is about 2% to about 3% by weight of the skin care formulation, such as about 2.0%, about 2.1%, about 2.2%, about 2.3%, about 2.4%, about 2.5%, about 2.6%, about 2.7%, about 2.8%, about 2.9%, or about 3.0%. In some embodiments, the glycerin is about 2.6% by weight of the skin care formulation.

Hyaluronic Acid

Hyaluronic acid or salt thereof (such as sodium hyaluronate) may hydrate dry or aged skin and help reduce wrinkles. It may also help to lock in moisture and increases skin elasticity. Skin aging is also associated with loss of skin moisture. Hyaluronan or hyaluronic acid (HA), a glycosaminoglycan (GAG) with a unique capacity to bind and retain water molecules may be an important molecule involved in skin moisture. HA belongs to the extracellular matrix (ECM) molecules. As a member of the GAG family, hyaluronic acid (HA) renders normal skin plump, soft and hydrated, and are believed to assist in maintaining proper salt and water balance and can bind 1000 times its weight in water. HA encompasses a large volume of water giving solutions high viscosity, even at low concentrations. The synthesis of HA increases during tissue injury and wound healing and HA regulates several aspects of tissue repair, including activation of inflammatory cells to enhance immune response and the response to injury of fibroblasts and epithelial cells.

The hyaluronic acid or salt thereof may be used as a final thickening agent for the present formulation. Commercial products (e.g., CAS Reg. Nos. 9004-61-9, 9067-32-7, 31799-91-4, or 149368-06-9) may be used. The hyaluronic acid or salt thereof may be present in an amount of about 0.1% to about 2% by weight of the skin care formulation. In some embodiments, the hyaluronic acid or salt thereof is about 0.1% to about 1.5% by weight of the skin care formulation, such as about 0.1% to about 1.5%, about 0.1% to about 1.0%, about 0.2% to about 1.0%, about 0.3% to about 1.0%, about 0.4 to about 1.0%, about 0.5% to about 1.5%, about 0.5% to about 1.0%, or about 0.5% to about 0.8%. In some embodiments, the hyaluronic acid or salt thereof is about 0.5% to about 1.0% by weight of the skin care formulation, such as about 0.5%, about 0.6%, about 0.7%, about 0.8%, about 0.9%, or about 1.0%.

Water

The ingredients of the present formulation may be dissolved or suspended in water as a carrier. For example, the prepared formulation may be in a form of a serum, a cream, or a lotion. The water may be distilled water from steam distillation. The water may be in an amount by weight that is the balance of the formulation after other ingredients are accounted for, the total weight percent being 100%. The water may be present in an amount of about 70% to about 95% by weight of the skin care formulation. In some embodiments, the water is about 75% to about 95% by weight of the skin care formulation, such as about 75% to about 90% or about 80% to about 90%. In some embodiments, the water is about 75% to about 90% by weight of the skin care formulation, such as about 75%, about 80%, about 85%, about 86%, about 87%, about 88%, about 89%, or about 90%. In some embodiments, the water is about 87% by weight of the skin care formulation.

The present formulation may comprise at least one additional ingredient. In some embodiments, the present formulation further comprises at least one addition ingredient selected from the group consisting of a moisturizer, an oil, a skin firming agent, an antioxidant, an emollient, and a fragrance. In some embodiments, the skin care formulation further comprises a skin tinting ingredient (such as spray tan liquid, tanning solution, or fake tanning).

Moisturizer

The moisturizer may retain moisture on a skin. Suitable moisturizers include, for example, polyols and polyethers (such as ethylhexylglycerin, caprylyl glycol, pentylene glycol, butylene glycol, or propylene glycol), amino acids (such as serine, proline, alanine, glutamate, or arginine), sugars and polysaccharides (such as glucose, isomerate saccharide, sorbitol, pentaerythritol, inositol, xylitol, or sorbitol), sorbitans (such as sorbitan distearate), lecithin, long chain alcohols (such as cetearyl alcohol or stearyl alcohol), glycerides (such as glyceryl monostearate), waxes of vegetable origin (such as candelilla wax (*Euphorbia cerifera*), carnauba wax (*Copernicia cerifera*)), *Aloe vera*, or a combination thereof.

In some embodiments, the moisturizer comprises *Aloe vera* (e.g., CAS Reg. No. 94349-62-9). For example, pure natural liquid derived from the hollow interior of the leaves of the *Aloe* plant (*Aloe barbadensis* Miller) may be used. The moisturizer (e.g., *Aloe vera*) may be used as a potent moisturizer, invigorating and soothing agent, and may improve the appearance of aging and dry skin. The moisturizer (e.g., *Aloe vera*) may be present in an amount of about 1% to about 15% by weight of the skin care formulation. In some embodiments, the moisturizer (e.g., *Aloe vera*) is about 1% to about 10% by weight of the skin care formulation, such as about 2% to about 10% or about 5% to about 10%. In some embodiments, the moisturizer (e.g., *Aloe vera*) is about 5% to about 10% by weight of the skin care formulation, such as about 5%, about 6%, about 7%, about 8%, about 9%, or about 10%. In some embodiments, the moisturizer (e.g., *Aloe vera*) is about 7% by weight of the skin care formulation.

Antioxidant

The antioxidant may be, for example, a free radical scavenger, an anti-atmospheric pollution agent, or a combination thereof. Suitable antioxidant may include, for example, tea extract, vitamin C and derivatives thereof, ferulic acid, retinol, resveratrol, curcumin, and combinations thereof. In some embodiments, the antioxidant comprises vitamin C or a derivative thereof. In some embodiments, the antioxidant comprises 3-glyceryl ascorbate (e.g., CAS Reg. No. 1120360-11-3), a derivative produced by binding vitamin C (ascorbic acid) to glycerin. This type of vitamin C may cause only minor irritation while retaining effective free radical protection, which may be used to achieve skin lightening and reduction (or evening) of age spots and pigmentation. This type of vitamin C may provide enhanced moisturizing and antioxidant properties when compared with ascorbic acid.

The antioxidant (e.g., 3-glyceryl ascorbate) may be present in an amount of about 0.1% to about 2% by weight of the skin care formulation. In some embodiments, the antioxidant (e.g., 3-glyceryl ascorbate) is about 0.1% to about 1% by weight of the skin care formulation, such as about 0.1% to about 0.8%, about 0.1% to about 0.5%, or about 0.2% to about 0.4%. In some embodiments, the antioxidant (e.g., 3-glyceryl ascorbate) is about 0.1% to about 0.5% by weight of the skin care formulation, such as about 0.1%, about 0.2%, about 0.3%, about 0.4%, or about 0.5%. In some embodiments, the antioxidant (e.g., 3-glyceryl ascorbate) is about 0.3% by weight of the skin care formulation.

Skin Firming Agent

The skin firming agent may have anti-wrinkle and/or anti-aging effects. Suitable skin firming agents include, for example, extracts or hydrolyzed extracts of *Vitis vinifera, Rosa canina, Curcuma longa, Theobroma cacao, Ginkgo biloba, Leontopodium, alpinum* or *Dunaliella salina* among others, palmitoyl pentapeptide-4, palmitoyl tetrapeptide-7, palmitoyl oligopeptide, palmitoyl tripeptide-5, or combinations thereof. In some embodiments, the skin firming agent comprises palmitoyl tripeptide-5.

Palmitoyl tripeptide-5 (e.g., CAS Reg. No. 623172-56-5) is a fragment of Thrombospondin I (TSP-1) presenting the sequence, N-(1-oxohexadecyl)-L-lysyl-L-valyl-L-lysine. Palmitoyl tripeptide-5 is proposed to reduce metalloproteases (MMP's) expression and pro-inflammatory cytokine syntheses, causing vasodilation and capillary permeability. It is used in anti-aging cosmetic products, due to its ability to reduce MMP'S and promote the synthesis of type I and type II collagen from extracellular matrix, as well as for inhibiting melanin production by reducing tyrosinase activity. Palmitoyl tripeptide-5 also may activate tissue growth factor (TGF-beta), which is known to stimulate collagen synthesis in the skin. Palmitoyl tripeptide-5 thus may have good skin firming and moisturizing properties, improve the appearance of various type of wrinkles, and reduce appearance of stretch marks.

The skin firming agent (e.g., palmitoyl tripeptide-5) may have a concentration of about 1 μg/gram to about 20 μg/gram by weight of the skin care formulation, such as about 1 jag/gram to about 15 μg/gram, about 1 pig/gram to about 10 μg/gram, or about 5 μg/gram to about 10 μg/gram. In some embodiments, the skin firming agent (e.g., palmitoyl tripeptide-5) has a concentration of about 5 μg/gram to about 10 μg/gram by weight of the skin care formulation, such as about 5 pig/gram, about 6 μg/gram, about 7 μg/gram, about 8 μg/gram, about 9 jag/gram, or about 10 μg/gram. In some embodiments, the skin firming agent (e.g., palmitoyl tripeptide-5) has a concentration of about 7 μg/gram by weight of the skin care formulation Oil An oil may be used as a carrier of the present formulation. The oil may also have moisturizing property. Suitable oils include, for example, castor oil, sunflower oil, coconut oil, fractionated coconut oil palm oil, wheat germ oil, sweet almond oil, wild soybean oil, grape seed oil, avocado oil, or combinations thereof. In some embodiments, the oil comprises fractionated coconut oil or medium chain triglycerides (e.g., C6-C14 triglycerides, CAS Reg. No. 73398-61-5). Fractionated coconut oil is clear and odorless and may leave no greasy feeling on the skin. Further, fractionated coconut oil (mainly medium chain triglycerides) does not stain and easily washes out of sheets and clothing. Remarkably, the fractionated coconut oil does not become solid like regular coconut oil but keeps all the desired properties and has a long shelf life.

The oil (e.g., fractionated coconut oil) may be present in an amount of about 0.1% to about 2% by weight of the skin care formulation. In some embodiments, the oil (e.g., fractionated coconut oil) is about 0.1% to about 1% by weight of the skin care formulation, such as about 0.1% to about 0.8%, about 0.1% to about 0.5%, or about 0.2% to about 0.4%. In some embodiments, the oil (e.g., fractionated coconut oil) is about 0.1% to about 0.5% by weight of the skin care formulation, such as about 0.1%, about 0.2%, about 0.3%, about 0.4%, or about 0.5%. In some embodiments, the oil (e.g., fractionated coconut oil) is about 0.4% by weight of the skin care formulation.

Emollient

An emollient of the present formulation may include waxlike and lubricating substances that may prevent water loss and have a softening and soothing effect on the skin. Suitable emollient may include, for example, algae extract, bee wax, C12-C18 acid triglycerides, hydrogenated olive oil, pumpkin seed extract, *quinoa* oil, rapeseed oil, red algae, rice oil, rose hip oil, rutin, saccharide isomerate, safflower seed oil, sesame oil, shea butter, silicone, soy oil, soya sterol, or squalene. In some embodiments, the emollient comprises squalene, rose hip oil, or a combination thereof Squalane (e.g., CAS Reg. No. 111-01-3) is a plant-based emollient derived from plant sugars (e.g., sugar cane). Squalane occurs naturally in the lipidic layers of the skin and prevents moisture loss while restoring the skin's suppleness and flexibility. Squalane is highly resistant to oxidation and has a high affinity to skin cells due to its skin-identical structure.

Rose hip oil (e.g., CAS Reg. No. 8007-01-0) is an oil extracted from the seeds of the rose hip or wildrose. Rose hip oil may contain high amount of linoleic and linolenic essential fatty acids which are key components of epidermal skin cells. Rose hip oil may have anti-aging effect due to its activity as PPAR-α agonist. PPAR-α is involved in inflammatory processes since its activation leads to an inhibition of pro-inflammatory genes expression like matrix metalloproteases (MMTP). Rose hip oil also may be rich in antioxidants that may help fight inflammation, which may be useful in reducing the severity of eczema, improving inflammatory acne, and clearing up acne scars. Rose hip oil also may stimulate collagen and improve the appearance of fine lines and wrinkles.

The emollient (e.g., squalene or rose hip oil) each may be present in an amount of about 0.1% to about 2% by weight of the skin care formulation. In some embodiments, the emollient (e.g., squalene or rose hip oil) is each about 0.1% to about 1% by weight of the skin care formulation, such as about 0.1% to about 0.8%, about 0.1% to about 0.5%, or about 0.2% to about 0.4%. In some embodiments, the emollient (e.g., squalene or rose hip oil) is each about 0.1% to about 0.5% by weight of the skin care formulation, such as about 0.1%, about 0.2%, about 0.3%, about 0.4%, or about 0.5%. In some embodiments, the emollient (e.g., squalene or rose hip oil) is each about 0.4% by weight of the skin care formulation. In some embodiments, the skin care formulation comprises about 0.4% by weight squalene, about 0.4% by weight rose hip oil, or both.

Fragrance

The fragrance is a material that improves the odor of the formulation or the skin. Suitable fragrance may include, for example, chamomile essence, carnation essence, lemon balm essence, mint essence, cinnamon leaf essence, lime blossom essence, juniper berry essence, vetiver essence, frankincense essence, galbanum essence, labdanum essence, lavender essence, peppermint essence, or combinations thereof. In some embodiments, the fragrance comprises lavender essential oil.

Lavender essential oil (e.g., CAS Reg. No. 8000-28-0) may also have calming, anti-irritating, and antimicrobial properties that help soothe the skin. As a natural preservative, lavender essential oil added to the present formulations may inhibit bacterial growth (e.g., *Staphylococcus aureus*). The fragrance (e.g., lavender essential oil) may be present in an amount of about 0.05% to about 1% by weight of the skin care formulation. In some embodiments, the fragrance (e.g., lavender essential oil) is about 0.05% to about 0.5% by weight of the skin care formulation, such as about 0.05% to about 0.4%, about 0.05% to about 0.3%, or about 0.1% to about 0.3%. In some embodiments, the fragrance (e.g., lavender essential oil) is about 0.1% to about 0.3% by weight of the skin care formulation, such as about 0.1%, about 0.15%, about 0.2%, about 0.25%, or about 0.3%. In some embodiments, the fragrance (e.g., lavender essential oil) is each about 0.2% by weight of the skin care formulation.

The present formulation may be adjusted to accommodate for sensitive skin and moisturizer for oily skin. For example, the oil (e.g., fractionated coconut oil), the antioxidant (e.g., vitamin C), and/or the fragrance (e.g., lavender essential oil) may be omitted to reduce skin sensitivity and oils. For these formulations, the amounts of hyaluronic acid may be slightly increased to thicken the formulation and offset a watery finish caused by omission of certain oils (e.g., coconut oil, vitamin C oil, and lavender oil). Also, the amounts of silver water are slightly increased to provide increased skin benefits for these formulations.

In one embodiment, provided is a skin care formulation as described herein, comprising:
about 0.5 μg/gram to about 1.5 μg/gram silver nanoparticles and/or silver microparticles;
about 0.5% to about 1.5% by weight dl-alpha tocopheryl acetate;
about 2% to about 3% by weight glycerin;
about 0.5% to about 0.8% by weight hyaluronic acid or a salt thereof;
about 5% to about 10% by weight *Aloe vera* juice;
about 5 μg/gram to about 10 μg/gram palmitoyl tripeptide-5;
about 0.1% to about 0.5% by weight 3-glyceryl ascorbate;
about 0.1% to about 0.5% by weight fractionated coconut oil;
about 0.1% to about 0.5% by weight squalane;
about 0.1% to about 0.5% by weight rose hip oil;
about 0.1% to about 0.3% by weight lavender essential oil; and
about 75% to about 90% by weight water.

In a particular embodiment, the formulation comprises:
about 0.7 μg/gram to about 1.5 μg/gram silver nanoparticles and/or silver microparticles;
about 1.1% by weight dl-alpha tocopheryl acetate;
about 2.6% by weight glycerin;
about 0.6% by weight hyaluronic acid or a salt thereof;
about 7% by weight *Aloe vera* juice;
about 7 μg/gram palmitoyl tripeptide-5;
about 0.3% by weight 3-glyceryl ascorbate;
about 0.4% by weight fractionated coconut oil;
about 0.4% by weight squalane;
about 0.4% by weight rose hip oil;
about 0.2% by weight lavender essential oil; and
about 88% by weight water.

In another embodiment, provided is a skin care formulation as described herein, comprising:
about 0.5 μg/gram to about 2.0 μg/gram by weight silver nanoparticles and/or silver microparticles;
about 0.5% to about 1.5% by weight dl-alpha tocopheryl acetate;
about 2% to about 3% by weight glycerin;
about 0.5% to about 1.0% by weight hyaluronic acid or a salt thereof;
about 5% to about 10% by weight *Aloe vera* juice;
about 5 μg/gram to about 10 μg/gram by weight palmitoyl tripeptide-5;
about 0.1% to about 0.5% by weight squalane;
about 0.1% to about 0.5% by weight rose hip oil;
about 75% to about 90% by weight water.

In a particular embodiment, the formulation comprises:
about 0.7 μg/gram to about 2.0 μg/gram by weight silver nanoparticles and/or silver microparticles;
about 1.1% by weight dl-alpha tocopheryl acetate;
about 2.3% by weight glycerin;
about 0.8% by weight hyaluronic acid or a salt thereof;
about 7% by weight *Aloe vera* juice;
about 7 μg/gram by weight palmitoyl tripeptide-5;
about 0.4% by weight squalane;
about 0.4% by weight rose hip oil;
about 88% by weight water.

Preparation

The present formulation may be prepared by mixing the ingredients into a homogeneous product. In one aspect, the present disclosure provides a method of preparing the skin care formulation as described herein, the method comprising: mixing the silver nanoparticles and/or silver microparticles, vitamin E, glycerin, hyaluronic acid or a salt thereof, optionally one or more additional ingredients as described herein, and water to form the skin care formulation. The mixing may be carried out, for example, by using a mixer or blender.

In some embodiments, the method of preparing the skin care formulation comprises adding hyaluronic acid or a salt thereof to a mixture of silver nanoparticles and/or silver microparticles, vitamin E, glycerin, optionally one or more additional ingredients, and water. For example, the silver nanoparticles and/or silver microparticles (e.g., as a suspension in water or colloidal silver), vitamin E, glycerin, optionally one or more additional ingredients are mixed in water to form a mixture, and hyaluronic acid or a salt thereof is subsequently added to the mixture, thereby the mixture is thickened to form the skin care formulation.

In some embodiments, the silver nanoparticles and/or silver microparticles (e.g., as a suspension in water or colloidal silver), *Aloe vera*, water, and hyaluronic acid or a salt thereof are mixed to form a thickened mixtures. The thickened mixture is then allowed to sit for at least 4 hours (such as 8 hours, 12 hours, or overnight). Subsequently, vitamin E, glycerin, and optionally one or more additional ingredients (e.g., squalane, rose hip oil, palmitoyl tripeptide- 5, vitamin C, fractionated coconut oil, and lavender essential oil) are mixed with the thickened mixture to form the skin care formulation.

The silver water and lavender oil may both serve as natural preservatives. Advantageously, the present formulation may achieve extended shelf life without the need for additional preservative. For example, the present formulation may remain stable and maintain its skin care properties after being stored at room temperature for at least 90 days, including at least 6 months, at least 1 year, at least 2 years, or at least 3 years. In some embodiments, the serum formulation has a shelf life of at least 90 days without refrigeration.

Method

In another aspect, the present disclosure provides a method of treating a skin condition in a subject in need thereof the method comprising applying an effective amount of the skin care formulation of claim 1 to the skin of the subject.

The subject may be an animal or a human. The skin may include the topical skin of any part of the subject, such as facial, arm, shoulder, leg, torso (e.g., chest and back), neck, hand, foot, and genital skins.

The skin conditions may include, but are not limited to, any know results of aging, sun damage, wound, or skin disease. In some embodiments, the skin condition is aging, wrinkle, pigmentation, elasticity loss, moisture loss, sun damage, chaffing, dryness, sagging, climate damage, scars, burns, sores, abrasions, eczema, inflammatory dermatitis, skin cancer, or a combination thereof.

In yet another aspect, the present disclosure provides a method of rejuvenating, repairing, or improving aesthetic appearance of a skin of a subject in need thereof, the method comprising applying an effective amount of the skin care formulation as described herein to the skin of the subject The present formulations may be mild and useful on all skin types. In some embodiments, the formulation is made from all natural ingredients with natural preservatives. In some embodiments, the formulation may be modified (e.g., by removing antioxidant, oil, fragrance, or other ingredients) to reduce irritation for subjects with certain skin conditions or sensitivities (such as acne prone or rosacea prone skin). The formulation is applied as a thin layer on the surface of the skin anywhere on the body, including underarms and external genital skin. The formulation typically dries in 20-60 seconds after application. Advantageously, the fast drying of the present formulations may provide a lightweight, matte finish without a greasy feel on the skin.

The present formulations may be used as a base layer, onto which other skin care or cosmetic products may be applied. For example, once the present formulation is fully dry after application, other products such as daily lotions, sunscreens (e.g., with SPF 15-50), creams, and moisturizers may be applied over it. The present formulation may be applied anytime, such as in the morning, afternoon, evening, and at night. The formulation also may be applied without washing the skin (e.g., face wash).

Many known skincare products only address one or two skin issues. Remarkably, the present formulation may provide a full body, multi-purpose product with many benefits, not just focusing on a single skin problem (such as night eye wrinkle cream for crows feet). For example, the present formulation may be used by men or women as an all-in-one, whole body, multi-benefit, anti-aging and moisturizing product for every kind of skin anywhere on the body, including underarms and external genital skin. Advantageously, the formulations disclosed herein are not greasy or sticky after application and drying on the skin, providing a smooth barrier with a matte finish. The formulation may tighten the skin as it dries, providing a breathable covering or a barrier. The formulation also may allow additional moisture under it, absorbing and holding the moisture. For example, applying the formulation when skin is still wet (e.g., not towel dried from the shower) may capture the remaining water and extend the drying time but may increase the moisture on the skin by capturing and holding the water on the skin while the formulation dries. The formulation may maintain a matte, soft finish absorbing and holding environmental moisture on top of the skin renewably moisturizing it throughout the day, until it is all absorbed into the skin by the end of the day. For example, the formulation may be applied in the morning and does not cause obvious slimy feeling during showering at night before bed. The present formulation may essentially multiply its moisturizing effect, while maintaining its non-greasy matte nature, all day by re-moisturizing itself and continually pulling moisture out of the air and multiplying it on the surface of the skin until it is fully absorbed.

The present formulations may moisturize the skin and provide anti-aging properties to firm, tighten, reduce fine lines and plump wrinkles, and lighten dark spots, burns, scores, abrasions, and scars on the skin. The present formulations also may soften skin and facial hair (e.g., beards) and support the skin's natural elasticity. The present formulation also may be used to reduce skin irritations, such as those caused by sunburn, wind burn, burns, eczema, dry spots, scratches/rashes, and bug bites/stings.

The following non-limiting examples illustrate the compositions of the present disclosure and method of use thereof.

EXAMPLES

Example 1 Preparation of a Skin Care Formulation

Silver nanoparticles and/or silver microparticles were generated as a suspension in water (micro-particle colloidal silver water, with particle size of about 0.8 nm) using a Micro-Particle Colloidal Silver Generator (The Silver Edge, AZ) and steam distilled water. Typically, the suspension produced in a single batch contained silver nanoparticles and/or silver microparticles at 10 ppm-20 ppm. The distilled water was processed through steam distillation. Not all distilled water is processed the same and some silver generators require the distilled water to be created through the steam distillation process (e.g., Arrowhead Distilled water is not the same as Sprouts Distilled water). Once the silver water is generated, it is stored in a dark room at room temperature in amber glass bottles.

Commercial ingredients used herein included distilled water (e.g., from steam distillation), hyaluronic acid (sodium hyaluronate powder), *Aloe vera* pure juice, palmitoyl tripeptide-5, vitamin C oil (3-glyceryl ascorbate), glycerin (USP), coconut oil (fractionated, MCT), vitamin E oil (dl-alpha tocopheryl acetate), squalane oil (from sugarcane), rose hip oil, and lavender essential oil. The commercial ingredients were used according to supplier's safety data sheet.

Prior to mixing the ingredients, all working surfaces were sanitized (e.g., using bleach) and covered with paper towels. The tools (blender and blades, measuring cups, spatula, etc.) were sanitized with rubbing alcohol and then rinsed tools with water to remove any surface-dried isopropyl alcohol.

The surfaces and tools were then dried by air. Containers (e.g., bottles) were cleaned by blowing air and arranged in a row for pouring.

The ingredients were mixed in a clean blender with high-speed mixing (e.g., a center column of 3 blades for mixing). To the blender, water was added first, followed by *Aloe vera* water, then silver water, then the oils: squalane, rose hip oil, palmitoyl tripeptide-5, vitamin C oil, vitamin E oil, glycerin, fractionated coconut oil, and lavender oil. For the sensitive skin serum, the following oils are omitted in this oil phase: fractionated coconut oil, vitamin C oil, and lavender oil. Once all the oils are added, the blender was turned to medium-high speed to mix the ingredients for at least 1-2 minute. Once the oils and water were blended together and almost frothy, hyaluronic acid (HA) powder was for final thickening. The ingredients were then mixed by the blender at medium-high speed for at least 1-2 minutes. HA and other ingredients that have splashed up on the sides of the blender were scraped off by spatula and pushed back into the mixture. The ingredients were further mixed by the blender at medium-high speed (for example, mixing for at least 1-2 minute, then rest for 1-2 minutes, then mixing again for 1 minute, then rest, then mixing again for 1-2 minutes) until the mixture was thick and frothy, and not watery or chucky.

Alternatively, the formulation may be prepared by an overnight process. To the blender, water was added first, followed by *Aloe vera* water, then silver water, then the hyaluronic acid (HA) powder for thickening. This mixture was allowed to sit overnight (typically for at least 8 hours) to congeal into a gel-like substance. Next, the oils were added: squalane, rose hip oil, palmitoyl tripeptide-5, vitamin C oil, vitamin E oil, glycerin, fractionated coconut oil, and lavender oil. For the sensitive skin serum, the following oils are omitted in this oil phase: fractionated coconut oil, vitamin C oil, and lavender oil. The ingredients were then mixed by the blender at medium-high speed for at least 1-2 minutes. HA and other ingredients that have splashed up on the sides of the blender were scraped off by spatula and pushed back into the mixture. The ingredients were further mixed by the blender at medium-high speed (for example, mixing for at least 1-2 minute, then rest for 1-2 minutes, then mixing again for 1 minute, then rest, then mixing again for 1-2 minutes) until the mixture was thick and frothy, and not watery or chucky.

A first serum formulation was made according to Table 1.

TABLE 1

| Ingredient | Amount |
|---|---|
| Silver water (10-20 ppm) | ⅛ cup (1.01 oz) |
| Distilled water | 2 cups (16 oz) |
| Aloe Vera Pure Juice | ⅛ cup (1.01 oz) |
| Tripeptide-5 (palmitoyl) (about 1 mg/g in 60% glycerin and 40% water) | 1 teaspoon (0.16 oz) |
| Vitamin C Oil (3-glyceryl ascorbate) (30% vitamin C, 30% glycerin, 40% water) | 1 teaspoon (0.16 oz) |
| Glycerin, USP | ½ tablespoon (0.25 oz) |
| Coconut Oil (fractionated, MCT) | ¼ tablespoon (0.125 oz) |
| Hyaluronic Acid (Sodium Hyaluronate Powder) | 1.5 teaspoon (6.72 grams) |
| Vitamin E Oil (dl-alpha tocopheryl acetate) | ½ tablespoon (0.25 oz) |
| Squalane Oil (from sugarcane) | 1 teaspoon (0.16 oz) |
| Rose Hip Oil | 1 teaspoon (0.16 oz) |
| Lavender Essential Oil | ¼ teaspoon (0.04 oz) |

A second serum formulation was made according to Table 2.

TABLE 2

| Ingredient | Amount (grams) |
|---|---|
| Silver nanoparticles and/or silver microparticles | $380\text{-}760 \times 10^{-6}$ [a] |
| Water | 470 |
| Aloe Vera Pure Juice | 38 |
| Tripeptide-5 (palmitoyl) | $4 \times 10^{-3}$ [b] |
| Vitamin C Oil (3-glyceryl ascorbate) | 1.8 |
| Glycerin, USP | 14.2 |
| Coconut Oil (fractionated, MCT) | 2 |
| Hyaluronic Acid (Sodium Hyaluronate Powder) | 3 |
| Vitamin E Oil (dl-alpha tocopheryl acetate) | 6 |
| Squalane Oil (from sugarcane) | 2 |
| Rose Hip Oil | 2 |
| Lavender Essential Oil | 1 |

[a] net weight in 10-20 ppm water suspension.
[b] net weight in 1 mg/g solution in glycerin/water.

A third serum formulation (for sensitive skin) was made according to Table 3.

TABLE 3

| Ingredient | Amount |
|---|---|
| Silver water (10-20 ppm) | 3/16 cup (1.5 oz) |
| Distilled water | 2 cups (16 oz) |
| Aloe Vera Pure Juice | ⅛ cup (1.01 oz) |
| Tripeptide-5 (palmitoyl) (about 1 mg/g in 60% glycerin and 40% water) | 1 teaspoon (0.16 oz) |
| Glycerin, USP | ½ tablespoon (0.25 oz) |
| Hyaluronic Acid (Sodium Hyaluronate Powder) | 1.75 teaspoon (7.32 grams) |
| Vitamin E Oil (dl-alpha tocopheryl acetate) | ½ tablespoon (0.25 oz) |
| Squalane Oil (from sugarcane) | 1 teaspoon (0.16 oz) |
| Rose Hip Oil | 1 teaspoon (0.16 oz) |

A fourth serum formulation (for sensitive skin) was made according to Table 4.

TABLE 4

| Ingredient | Amount (grams) |
|---|---|
| Silver nanoparticles and/or silver microparticles | $420\text{-}840 \times 10^{-6}$ [a] |
| Distilled water | 471.6 |
| Aloe Vera Pure Juice | 38 |
| Tripeptide-5 (palmitoyl) | $4 \times 10^{-3}$ [b] |
| Glycerin, USP | 12.4 |
| Hyaluronic Acid (Sodium Hyaluronate Powder) | 4 |
| Vitamin E Oil (dl-alpha tocopheryl acetate) | 6 |
| Squalane Oil (from sugarcane) | 2 |
| Rose Hip Oil | 2 |

[a] net weight in 10-20 ppm water suspension.
[b] net weight in 1 mg/g solution in glycerin/water.

Compared to the first and second formulations, the amounts of hyaluronic acid in the third and fourth formulations were slightly increased to thicken the formulation and offset the omission of certain oils (coconut oil, vitamin C oil, and lavender oil) that will present with a watery finish without the addition of the additional thickening agent. Also, the amounts of silver water in the third and fourth formulations were slightly increased to provide increased skin benefits.

The formulation was poured into bottles once there were almost no bubbles resting on top. The bottles were then sealed and labeled. Some ingredients, such as silver water and vitamin C oil may break down in sunlight or during refrigeration. Non-plastic, amber color glass or UV sunblock finish was used for packaging. The shelf life of the present formulations is at least one (1) year but may last as long as three (3) years. In a microbiological test, a representative formulation (1.0 gram) was exposed to ambient temperature of 23.0±2.0° C. and was incubated at an incubation temperature of 30.0±2.0° C. or 36.0±1.0° C. for 2-4 days. The growth media were TSA (bacteria) and PDA (fungi). Dey/Engley (D/E) broth was used as neutralizer. The microbiological analysis results are shown in Table 5 (bacteria and fungi) and Table 6 (neutralization and recoverability analysis). The results showed that microbiological growth is kept at satisfactory level in the formulation.

TABLE 5

| Microorganism Type | Detection Media | CFU/g |
|---|---|---|
| Aerobic Bacteria | Tryptic Soy Agar | 365 |
| Yeast and Mold | Potato Dextrose Agar | <5 * |

* The limit of detection for this assay was 5 CFU/g for bacteria and fungi. Values of <5 indicate that microorganisms could not be detected in the submitted samples

TABLE 6

| Microorganism | Substance | Neutralization Validation Counts | Average NV Counts | Percent Recovery | Neutralization Scheme |
|---|---|---|---|---|---|
| B. subtilis | Control | 70    77 | 73.5 | N/A | 1:10 in |
| ATCC 6633 | Formulation | 119*    104* | 111.5 | 151.70% | Dey/Engley broth |
| P. aeruginosa | Control | 44    46 | 45 | N/A | 1:10 in |
| ATCC 9027 | Formulation | 56    36 | 46 | 102.22% | Dey/Engley broth |
| S. aureus | Control | 32    47 | 39.5 | N/A | 1:10 in |
| ATCC 6538 | Formulation | 52    34 | 43 | 108.86% | Dey/Engley broth |
| C. albicans | Control | 39    38 | 38.5 | N/A | 1:10 in |
| ATCC 10231 | Formulation | 39    42 | 40.5 | 105.19% | Dey/Engley broth |
| A. brasiliensis | Control | 71    52 | 61.5 | N/A | 1:10 in |
| ATCC 16404 | Formulation | 73    61 | 67 | 108.94% | Dey/Engley broth |

*The B. subtilis ATCC 6633 neutralization validation counts for the test substance were morphologically similar to the colonies present on the bacterial plates for the examination of the product, which may cause some variability in this data.

Example 2. Use of a Skin Care Formulation

The serum formulation is mild and can be used for all skin types. All ingredients are natural. People with certain skin conditions such as acne prone or rosacea prone skin may become irritated from the vitamin C and/or coconut oil, in which case a formulation for sensitive skin/moisturizer for oily skin is more suitable. The formulation is applied as a thin layer on the surface of the skin anywhere on the body including genitals. The formulation typically dries in 20-60 seconds after application. The novel drying effect provides a lightweight, matte finish that pulls the skin taut within 20-60 seconds and the applied formulation is non-greasy.

A representative formulation was applied as a thin layer after morning face wash/shower and before bed all over body, with special attention to back of the legs/bottom, face, neck, chest, elbows, and shoulders. The serum may be applied anytime, even without a prior face wash, e.g., while the user is on a trail. Skin test may be needed to ensure that the user is not allergic to the formulation. In some tests, the serum formulation was used as a base layer and other lotions or additional skin care products were applied over it for skin absorption. Some formulations may not provide SPF protection. Once the serum is fully dry and not damp or sticky (typically after 20-60 seconds), daily lotions, SPF, and moisturizers may be applied over it. If another product (e.g., lotion or SPF) are applied over the serum before the serum is dry, it may cause the product to be clumpy and sticky. Some formulations provided skin tinting (e.g., "fake" tan).

In one test, a female user having scarred and dented skin resulting from skin cancer and sun damage reported improvement or skin conditions after applying a representative formulation, which demonstrated the formulation's benefit in rejuvenating and repairing the skin.

In another test, users with acne-prone skin reported mild reaction and non-greasy feeling on the skin after applying a representative formulation.

In another test, a representative formulation was applied to the wounded skins of users suffering from wasp sting or bee sting. The user reported tightening of the wounded skin and improved healing without pain or swelling around the stung area.

In another test, a user having blisters and scars on hands and arms resulting from freezing applied a representative formulation to the affected skin areas. The formulation caused the affected areas to dry up and gradually fade away, which shows that the formulation can repair damaged skin and improve appearance of the skin.

In additional tests, the following results were obtained after the user applied a representative formulation to the skin:

1) After having her breast removed and not replaced from breast cancer, a female over 50 years old reported lightening of her mastectomy scar.
2) After a CO2 Laser resurfacing treatment, a female over 55 years old reported much faster healing time and an overall tighter feeling to the treated areas.
3) A female over 50 years old reported that the redness in her neck and chest was reduced significantly.
4) A female over 40 years old reported that the eczema on her hands was reduced to almost eliminated. In contrast, she previously tried many other skin treatment products without significant improvement.
5) A male over 20 years old, reported fast healing time and pain soothing when he used the formulation on his sunburned feet.
6) A female over 40 years old reported reduction of hormonal acne on her jaw line.
7) A female over 50 years old reported reduction of redness from roceasa on her face.
8) A female over 60 years old reported tighter leg skin and reduced creepy knees.

It is understood that the foregoing detailed description and accompanying examples are merely illustrative and are not to be taken as limitations upon the scope of the invention, which is defined solely by the following claims.

Various changes and modifications to the disclosed embodiments will be apparent to those skilled in the art. Such changes and modifications, including without limitation those relating to the substances, compositions, formulations, preparation process, or methods of use of the invention, may be made without departing from the spirit and scope thereof.

The invention claimed is:

1. A skin care formulation, consisting of:
   about 0.5 μg/gram to about 1.5 μg/gram silver nanoparticles and/or silver microparticles;
   about 0.5% to about 1.5% by weight dl-alpha tocopheryl acetate;
   about 2% to about 3% by weight glycerin;
   about 0.5% to about 0.8% by weight hyaluronic acid or a salt thereof;
   about 5% to about 10% by weight *Aloe vera* juice;
   about 5 μg/gram to about 10 μg/gram palmitoyl tripeptide-5;
   about 0.1% to about 0.5% by weight 3-glyceryl ascorbate;
   about 0.1% to about 0.5% by weight fractionated coconut oil;
   about 0.1% to about 0.5% by weight squalane;
   about 0.1% to about 0.5% by weight rose hip oil;
   about 0.1% to about 0.3% by weight lavender essential oil; and
   about 75% to about 90% by weight water.

2. The skin care formulation of claim 1, consisting of:
   about 0.70 μg/gram to about 1.5 μg/gram silver nanoparticles and/or silver microparticles;
   about 1.1% by weight dl-alpha tocopheryl acetate;
   about 2.6% by weight glycerin;
   about 0.6% by weight hyaluronic acid or a salt thereof;
   about 7% by weight *Aloe vera* juice;
   about 7 μg/gram palmitoyl tripeptide-5;
   about 0.3% by weight 3-glyceryl ascorbate;
   about 0.4% by weight fractionated coconut oil;
   about 0.4% by weight squalane;
   about 0.4% by weight rose hip oil;
   about 0.2% by weight lavender essential oil; and
   about 88% by weight water.

3. A skin care formulation, consisting of:
   about 0.5 μg/gram to about 2.0 μg/gram by weight silver nanoparticles and/or silver microparticles;
   about 0.5% to about 1.5% by weight dl-alpha tocopheryl acetate;
   about 2% to about 3% by weight glycerin;
   about 0.5% to about 1.0% by weight hyaluronic acid or a salt thereof;
   about 5% to about 10% by weight *Aloe vera* juice;
   about 5 μg/gram to about 10 μg/gram by weight palmitoyl tripeptide-5;
   about 0.1% to about 0.5% by weight squalane;
   about 0.1% to about 0.5% by weight rose hip oil; and
   about 75% to about 90% by weight water.

4. The skin care formulation of claim 3, consisting of:
   about 0.7 μg/gram to about 2.0 μg/gram by weight silver nanoparticles and/or silver microparticles;
   about 1.1% by weight dl-alpha tocopheryl acetate;
   about 2.3% by weight glycerin;
   about 0.8% by weight hyaluronic acid or a salt thereof;
   about 7% by weight *Aloe vera* juice;
   about 7 μg/gram by weight palmitoyl tripeptide-5;
   about 0.4% by weight squalane;
   about 0.4% by weight rose hip oil; and
   about 88% by weight water.

5. A method of preparing the skin care formulation of claim 1, the method comprising: mixing the silver nanoparticles and/or silver microparticles, dl-alpha tocopheryl acetate, glycerin, hyaluronic acid or a salt thereof, *Aloe vera* juice, palmitoyl tripeptide-5, 3-glyceryl ascorbate, fractionated coconut oil, squalene, rose hip oil, lavender essential oil, and water to form the skin care formulation.

6. The method of claim 5, comprising adding hyaluronic acid or a salt thereof to a mixture of silver nanoparticles and/or silver microparticles, vitamin E, glycerin, *Aloe vera* juice, palmitoyl tripeptide-5, 3-glyceryl ascorbate, fractionated coconut oil, squalene, rose hip oil, lavender essential oil, and water.

7. A method of treating a skin condition in a subject in need thereof, the method comprising applying an effective amount of the skin care formulation of claim 1 to the skin of the subject.

8. The method of claim 7, wherein the skin condition is aging, wrinkle, pigmentation, elasticity loss, moisture loss, sun damage, chaffing, dryness, sagging, climate damage, scars, burns, sores, abrasions, eczema, inflammatory dermatitis, skin cancer, or a combination thereof.

9. A method of moisturizing, rejuvenating, repairing, or improving aesthetic appearance of a skin of a subject in need thereof, the method comprising applying an effective amount of the skin care formulation of claim 1 to the skin of the subject.

10. A method of preparing the skin care formulation of claim 3, the method comprising: mixing the silver nanoparticles and/or silver microparticles, dl-alpha tocopheryl acetate, glycerin, hyaluronic acid or a salt thereof, *Aloe vera* juice, palmitoyl tripeptide-5, squalene, rose hip oil, and water to form the skin care formulation.

11. The method of claim 10, comprising adding hyaluronic acid or a salt thereof to a mixture of silver nanoparticles and/or silver microparticles, vitamin E, glycerin, *Aloe vera* juice, palmitoyl tripeptide-5, squalene, rose hip oil, and water.

12. A method of treating a skin condition in a subject in need thereof, the method comprising applying an effective amount of the skin care formulation of claim 3 to the skin of the subject.

13. The method of claim 12, wherein the skin condition is aging, wrinkle, pigmentation, elasticity loss, moisture loss, sun damage, chaffing, dryness, sagging, climate damage, scars, burns, sores, abrasions, eczema, inflammatory dermatitis, skin cancer, or a combination thereof.

14. A method of moisturizing, rejuvenating, repairing, or improving aesthetic appearance of a skin of a subject in need thereof, the method comprising applying an effective amount of the skin care formulation of claim 3 to the skin of the subject.

* * * * *

UNITED STATES PATENT AND TRADEMARK OFFICE
CERTIFICATE OF CORRECTION

PATENT NO. : 12,194,120 B2
APPLICATION NO. : 17/890947
DATED : January 14, 2025
INVENTOR(S) : Heidi Callender et al.

It is certified that error appears in the above-identified patent and that said Letters Patent is hereby corrected as shown below:

In the Specification

Column 4, Lines 49-50, "0.9 jag/gram" should be --0.9 μg/gram--.

Column 4, Line 50, "1.0 jag/gram" should be --1.0 μg/gram--.

Column 4, Line 51, "1.4 jag/gran" should be --1.4 μg/gram--.

Column 7, Line 52-53, "1 jag/gram" should be --1 μg/gram--.

Column 7, Line 53, "1 pig/gram" should be --1 μg/gram--.

Column 7, Line 58, "5 pig/gram" should be --5 μg/gram--.

Column 7, Line 59, "9 jag/gram" should be --9 μg/gram--.

Column 8, Line 50, "(MMTP)" should be --(MMP)--.

Signed and Sealed this
Eighteenth Day of March, 2025

Coke Morgan Stewart
*Acting Director of the United States Patent and Trademark Office*